United States Patent
Campana et al.

(10) Patent No.: US 7,300,915 B2
(45) Date of Patent: Nov. 27, 2007

(54) USE OF ERYTHROPOIETIN AND ERYTHROPOIETIN MIMETICS FOR THE TREATMENT OF NEUROPATHIC PAIN

(75) Inventors: W. Marie Campana, Solana Beach, CA (US); Robert R. Myers, Carlsbad, CA (US)

(73) Assignee: The Regents of the University of California, Oakland, CA (US)

( * ) Notice: Subject to any disclaimer, the term of this patent is extended or adjusted under 35 U.S.C. 154(b) by 147 days.

(21) Appl. No.: 10/455,697

(22) Filed: Jun. 5, 2003

(65) Prior Publication Data

US 2004/0018978 A1 Jan. 29, 2004

Related U.S. Application Data

(60) Provisional application No. 60/386,286, filed on Jun. 5, 2002.

(51) Int. Cl.
*A61K 38/00* (2006.01)
*A61K 38/18* (2006.01)
*C07K 14/505* (2006.01)

(52) U.S. Cl. .............................. 514/2; 530/397; 530/399

(58) Field of Classification Search .................... 514/2, 514/8; 530/397
See application file for complete search history.

(56) References Cited

U.S. PATENT DOCUMENTS

| | | | |
|---|---|---|---|
| 5,835,382 A | 11/1998 | Wilson et al. | |
| 6,045,830 A | 4/2000 | Igari et al. | |
| 6,221,608 B1 | 4/2001 | Middleton et al. | |
| 6,310,078 B1 | 10/2001 | Connolly et al. | |
| 6,319,499 B1 | 11/2001 | Elliott | |
| 6,333,306 B1 * | 12/2001 | Lehmann ........................ | 514/8 |
| 6,340,742 B1 | 1/2002 | Burg et al. | |
| 6,489,293 B1 | 12/2002 | Sykowski et al. | |
| 2003/0104988 A1 * | 6/2003 | Brines et al. .................. | 514/8 |

OTHER PUBLICATIONS

Wells, Additivity of Mutational Effects in Proteins. Biochemistry vol. 29/37:8509-8517 (1990).*
Vinik, A. Clinical review: use of antiepileptic drugs in the treatment of painful diabetic neuropathy. The Journal of Clinical Endocrinology and Metabolism 90(8):4936-4945 (2005).*
Eastman, Richard C. Neuropathy in Diabetes. Chapter 15 (pp. 339-348) from Diabetes in America. 2nd Edition (1995).*
Knowles et al. Painful diabetic neuropathy:assessment and treatment-Clinical. Journal of Diabetes Nursing, pp. 1-9. (Jul.-Aug. 2002).*
Veves, A et al. Painful neuropathy and foot ulceration in diabetic patients. Abstract, Diabetes Care 16(8):1187-9 (Aug. 1993).*
Tsigos, C et al. Plasma norepinephrine in sensory diabetic polyneuropathy. Abstract, Diabetes Care 16(5):722-7 (May 1993).*
Veves, A. et al. Differences in peripheral and autonomic nerve function measurements in painful and painless neuropathy. A clinical study. Abstract, Diabetes Care 17(10):1200-2 (Oct. 1994).*
Britland, ST, et al. Acute and remitting painful diabetic polyneuropathy: a comparison of peripheral nerve fibre pathology. Abstract, Pain 48(3):361-70 (Mar. 1992).*
Britland, ST et al. Association of painful and painless diabetic polyneuropathy with different patterns of nerve fiber degeneration and regeneration. Abstract, Diabetes 39(8):898-908 (Aug. 1990).*
Young, RJ et al. Variable relationship between peripheral somatic and autonomic neuropathy in patients with different syndromes of diabetic polyneuropathy. Abstract, Diabetes 35(2):192-7 (Feb. 1986).*
Tsigos, C et al. Discrimination between painful and painless diabetic neuropathy based on testing of large somatic nerve and sympathetic nerve function. Abstract, Diabet. Med. 9(4):359-65 (May 1992).*
Fink et al. Small-fiber neuropathy:Answering the burning questions. Science of Aging Knowledge Environment. vol. 2006, Issue 6, p.e7; pp. 1-9 (Mar. 8, 2006).*
Brines et al., Erythropoietin crosses the blood-brain barrier to protect against expermental brain injury. Proc.Natl.Acad.Sci.USA 97:10526-10531, 2000.
Campana et al., Prosapeptide activates the MAPK pathway by a G-protein dependent mechanism essential for enhanced sulfatide synthesis by Schwann cell FASEB J. 12:307-314, 1998.
Campana et al., Identification of a neurotrophic sequence in erythropoietin. Int. J. Mol. Med. 1:235-241.1998.
Campana et al., Erythropoietin and erythropoietin receptors in the peripheral nervous system: changes after nerve injury. FASEB J. express article 10.1096. 2001.
Celik et al., Erythropoietin prevents motor neuron apoptosis and neurological disability in experimental spinal cord ischeimic injury. Proc.Natl.Acad.Sci.USA 99:2258-63, 2002.
Digicaylioglu and Lipton, Erythropoietin-mediated neuroprotection invovles cross-talk between Jak2 and Nf-kB signalling cascasesNature 412:641-7, 2001.
Egrie et al., Pharmacokinetics of recombinant human erythropoietin (rHuEpo) administered to hemodialysis patient. Kidney Int., 33:262, 1998.
Ehrenreich et al., Erythropoietin therapy for acute stroke is both safe and beneficial. Mol.Medicine 8:495-505, 2002.

(Continued)

*Primary Examiner*—Marianne P. Allen
*Assistant Examiner*—Regina M. DeBerry
(74) *Attorney, Agent, or Firm*—Mandel & Adriano (57) ABSTRACT

Erythropoietin (Epo), a member of the cytokine superfamily, is a pluripotent molecule that is involved in a number of signal transduction pathways that include the stimulation of the production of red blood cells and the protection of the central nervous system from acute injury and ischemia. The invention is the discovery of Epo and the Epo receptor in the peripheral nervous system where it can act as a neuroprotective agent. The invention is also a method of use for the treatment of neuropathic pain and to increase the rate of healing from nerve injury comprising administration of Epo.

16 Claims, 5 Drawing Sheets

OTHER PUBLICATIONS

Fisher, Erythropoietin: Physiology and pharmacology update. Exp Biol. Med. 288:1-14, 2003.

Hargreaves et al., New and sensitive method for measuring thermal nociception in cutaneous hyperalgesia. Pain 32:77-78, 1988.

Igarashi et al., Exogenous tumor necrosis factor-alph mimics nucleus pulposus-induced neuropathology. Spine 25:2975-80, 2000.

Junk et al., Erythropoietin administration protects retinal neurons from acute ischemia-reperfusion injury. Proc.Natl.Acad.Sci.USA 99:10659-64, 2002.

Konishi et al. Trophic effect of erythropoietin and other hematopoietic factors on central cholinergic neurons in vitro and in vivo. Brain.Res. 609:29-35.1993.

MacDougall, Novel erythropoiesis stimulating protein. Semin. Nephrol. 20:375-381, 2000.

Marti et al. neuroprotection and angiogenesis: Dual role of erythropoietin in brain ischemia. New. Physiol. Sci. 15:225-229. 2000.

Masuda et al. Functional erythropoietin receptor of the cells with neural characteristics. J.Biol.Chem. 268:11208-16.1993.

Morishita et al., Erythropoietin receptor is expressed in rat hippocampal and cerebral cortical neurons, and epo prevents in vitro . . . Neurosci, 76:105-116. 1997.

Sakanaka et al., In vivo evidence that erythropoietin protects neurons from ischemic damage. Proc. Natl. Acad. Sci. USA 95:4635-4640, 1998.

Sirén et al., Erythropoiesis prevents neuronal apoptosis after cerebral ischemia and metabolic stress. Proc.Natl.Acad.Sci.USA 98:4004-09, 2000.

Wagner R. and Myers RR., Endoneurial injection of TNF-alpha produces neuropathic pain behaviors. Neuroreport 7:2897-901, 1996.

* cited by examiner

TABLE 1
Effects of rhEPO on weight, hematocrit and blood pressure after 14 days

| Animal Group | D0 weight | D14 weight | D14 Hematocrit | D5 Blood Pressure | D14 Blood Pressure |
|---|---|---|---|---|---|
| Sham Vehicle | 221 ± 11.52 | 222 ± 6.7 | N/A | N/A | N/A |
| Crush Vehicle | 221 ± 7.18 | 212 ± 5.3 | 43 ± 1.96 | 88 ± 11.3 | 91 ± 8.48 |
| Crush rhEPO | 220 ± 11.9 | 212 ± 9.22 | 77 ± .88* | 101 ± 1.41 | 101 ± 0.71 |

\* indicates a significant difference ($p<0.05$) between crush vehicle and crush rhEPO hematocrits

TABLE 2
Quantification of neuronal cell bodies of injured and uninjured adult rat DRG immunoreactive for the Erythropoietin Receptor

| Model | Total Neurons Counted | Independent DRG samples | % EpoR Positive (mean ± SEM) |
|---|---|---|---|
| Uninjured | 3503 | N=12 | 89.68 ± 1.55 |
| CCI | 3856 | N=12 | 86025 ± 1.53 |
| Crush | 2365 | N=8 | 75.72 ± 3.83** |

\*\*$p< 0.01$ Differences between D0 and D7

Figure 1A- Thermal Hyprealgesia

Figure 1B- Mechanical Allodynia

Figure 2A Mechanical Allodynia (threshold, gram pressure weight

Figure 2B- % DRG Apoptosis

Figure 2C- % Spinal Neuronal Apoptosis

USE OF ERYTHROPOIETIN AND ERYTHROPOIETIN MIMETICS FOR THE TREATMENT OF NEUROPATHIC PAIN

CROSS-REFERENCES TO RELATED APPLICATIONS

This application claims the benefit of priority of U.S. provisional application Ser. No. 60/386,286 filed Jun. 5, 2002 which is incorporated herein by reference in its entirety.

GOVERNMENT SUPPORT

This research was supported by National Institutes of Health Grant NS18715 and NS041983-01A2. The government may have certain rights in this invention.

SEQUENCE LISTING

A sequence listing conforming to the requirements of 37 C.R.F. §1.821 is submitted herewith and hereby incorporated by reference.

BACKGROUND OF THE INVENTION

Neuropathic pain results from injury to a nerve rather than injury to a tissue. Pain from tissue injury is typically short lived and is usually limited to the period of tissue repair. This pain can be readily treated by any of a number of over the counter and prescription analgesics well known to those skilled in the art. In contrast, neuropathic pain can develop days or even months after traumatic nerve injury and the pain is typically long-lasting or chronic. Moreover, neuropathic pain can occur spontaneously or as a result of stimulation that is normally not painful.

Neuropathic pain is caused by both trauma and disease. For example, trauma nerve compression or crush and traumatic injury to the spinal cord or brain are common causes. During nerve healing and regeneration, neuromas can result in pain due to abnormal nerve regeneration. Nerve crush and compression can be caused by the growth of tumors or other abnormalities, resulting in pain. Additionally, neuropathies may be caused by a number of diseases and disease conditions including diabetes mellitus, chemotherapy treated cancer, post herpetic neuralgia, lumbar radiculopathy, ischemia, vasculitis, alcoholism, HIV and some vitamin deficiencies.

Neuropathic pain is not readily treatable by common analgesics. Current therapies typically have severe side effects including, for example, cognitive changes, sedation, nausea and, with narcotic drugs, addiction. As neuropathic pain is frequently related to other disease states, individuals may suffer from adverse drug interactions or be less able to tolerate the side effects of the drugs. These limitations in current therapies can result in depression and a decreased quality of life in those suffering from neuropathic pain.

After nerve injury, peripheral nerves begin to degenerate, starting at the site of injury and progressing to the nerve terminal. This process, Wallerian degeneration, is essential for regeneration and has been characterized extensively in an animal model of neuropathic pain, chronic constriction injury (CCI). During degeneration, the axoplasm gradually disintegrates and the axolemma fragments. Schwann cells and macrophages phagocytose myelin debris. This process activates a secretion of a series of known and unknown factors including interferons, tumor necrosis factor-alpha (TNF-α), nerve growth factor (NGF) and interleukins. These agents directly influence the structure and function of both adjacent and distal tissue, including the induction of apoptosis in a number of peripheral cells and production of trophic factors required for regeneration of both nerve and peripheral cells.

Development of increased sensitivity to noxious stimuli (hyperalgesia) in nerve injured animals arises from a complex series of events. These include: 1) early electrophysiological events like "injury discharge" that alters neuronal influx of calcium to activate kinases such as protein kinase A and C, and the extracellular regulated kinases (ERK 1/2), leading to proliferation, chemotaxis and other cellular activation at the injury site and physiological changes at the cell body; and 2) intermediate events such as retrogradely transported injury signals that include target derived factors/cytokines. These events can occur from hours to weeks after nerve injury resulting in pain and hypersensitivity for the duration of the process. Studies using axoplasm extruded from injured ends of axons and injected into the cell bodies of uninjured sensory neurons found that the axoplasm elicited the same increase in excitability a day later in the uninjured neurons as those produced by axonal injury. In contrast, axoplasm from uninjured neurons had no effect, demonstrating expression and/or activation of factors in the injured nerve.

Studies have demonstrated that the factors secreted and activated by injured nerves and peripheral cells are responsible for the establishment of neuropathic pain. Trophic factors such as NGF and TNF-α are produced by Schwann cells and invading macrophages after nerve injury and are correlated with onset of hyperalgesia. Interestingly, both of these factors also have positive regenerative effects on damaged nerves, but cause pain in both undamaged and damaged nerves and result in thermal hyperalgesia and mechanical allodynia in non-injured animals. Similar responses are seen in humans. NGF induces changes in phenotype of sensory neurons by upregulating growth related molecules which may lead to hyperinnervation and amplifying sensory input by increasing neuropeptide levels. One key neuropeptide is substance P, which elicits pain through the neurokinin receptor (NK-1) receptor. NGF can induce the release of substance P which is known to be released in through activation of an unknown tyrosine kinase pathway which is likely mediated by cytokine-induced signaling. These complex and redundant pleiotrophic signaling pathways make the treatment of neuropathic pain, without the inhibition of neuronal healing, a substantial challenge.

SUMMARY OF THE INVENTION

The invention is the discovery of the expression of erythropoietin (Epo) and erythropoietin receptor (EpoR) in the peripheral nervous system and their neuroprotective effect in the peripheral nervous system (PNS). Epo protects Schwann cells from apoptosis and downregulation of EpoR activity is associated with neuronal apoptosis in the dorsal root ganglia (DRG) associated with experimentally injured peripheral nerves. The expression levels of both Epo and EpoR are altered upon nerve injury. Epo activates signaling molecules associated with increased proliferation, anti-apoptosis and neuropathic pain. The presence of Epo and EpoR in peripheral nerves provides potential points of intervention for the development of neuroprotective agents and the treatment of nerve injury and neuropathic pain.

The invention is the discovery that the administration of Epo after peripheral nerve injury decreases nerve degeneration and pain, and increases the rate of recovery. This discovery provides a method for the treatment of nerve injury and neuropathic pain by the use of Epo and Epo mimetics.

The invention is a method for protection of the PNS and the treatment of neuropathic pain comprising the systemic administration of a therapeutic dose of Epo. Treatment may be short or long term depending on the nature of the nerve injury or source of neuropathic pain. Epo has long been used for the treatment of various forms of anemia, such compounds are well known to those skilled in the art and are recognized as safe for use in most individuals. Epo can be used for the protection and treatment of peripheral nerve injury caused by any injury or insult and is not limited for use for treatment of injuries resulting from nerve crush or other traumatic, acute injury and neuroppathic pain caused by disease.

BRIEF DESCRIPTION OF THE DRAWINGS

Table 1 shows blood pressure and hematocrit in animals in response to treatment with rhEpo; and Table 2 shows the proportion of EpoR immunostaining in DRG cell bodies after CCI and SNC.

DETAILED DESCRIPTION AND PREFERRED EMBODIMENTS

Erythropoietin, a member of the cytokine superfamily, is a glycoprotein that supports survival, proliferation and differentiation of erythroid precursors. Originally, Epo was known for erythropoeisis, but it is now evident that Epo is a multifunctional trophic factor. Masuda et al. (1993) *J. Biol. Chem.* 268:11208-16, established Epo as a potent trophic factor on neural cells by showing a rapid increase in cytosolic calcium and intracellular monamines in PC12 cells after Epo treatment. Epo-enhanced production of choline acetyltransferase (ChAT) activity in primary septal neurons and cholinergic SN6 cells expanded its known effects (Konishi et al. (1993) *Brain. Res.* 609:29-35). Epo is known to support survival of septal cholinergic neurons in the central nervous system (CNS) in adult rats with fimbria-fornix transections. It has also been shown that an increase in ChAT activity in SK-N-MC cells, enhanced sprouting of NS20Y cells and motor endplates, and increased ERK1/2 phosphorylation in PC12 cells (Campana et al. (1998) *Intl. J. Molec. Med.* 1:235-241).

The effects of Epo on the brain were surprising because of its molecular weight. Epo, originally believed to be produced only in the kidney, would not be predicted to cross the blood-brain barrier due to its size. It was believed that the Epo found in brain was produced exclusively locally. Initial studies on the effect of Epo on neuronal injury in the brain and CNS involved the injection of Epo directly into rodent brain. However, Brines et al., *Proc. Natl. Acad. Sci. USA* 97:10526-10531, 2000, demonstrated that systemic injection of Epo up to six hours before brain injury, both focal ischemic stroke and blunt injury, had a neuroprotective effect similar to intraventricular (IT) injection into the brain. Time course experiments demonstrated that Epo acted as a neuroprotective agent in the CNS. Seizures induced by kainate, treatment with Epo up to three days before administration of the drug decreased the severity of the seizures. However, administration of Epo 30 minutes before or anytime after administration of kainate did not ameliorate seizures. The requirement for pretreatment for therapeutic value of Epo in the CNS was confirmed by Sirén et al. using a model of cerebral ischemia and metabolic stress (*Proc. Natl. Acad. Sci. USA* 9:4004-09, 2000). Neuroprotection could be conferred by a single dose of Epo administered three days before neuronal insult. It is believed that pretreatment induces a gene expression program that can be sustained for at least three days in the absence of Epo. Post treatment of Epo three hours after brain injury had a similar protective effect as compared to pretreatment with Epo, yet the protective effect was lost by 9 hours. However, more recently, high does of rhEpo (33,000 IU/50 mL/30 min) given to patients for 3 days after stroke were associated with improvement in follow-up and outcome scales (Ehrenreich et al., *Mol. Medicine* 8:495-505, 2002) demonstrating efficacy of rhEpo administered post injury. It is unlikely that the protective effect is due to an increased oxygen capacity of the blood resulting in decreased hypoxia of the tissue due to the low levels and short lead time of Epo administration required for efficacy of treatment in the CNS.

The invention is the discovery of the presence of Epo and EpoR in the PNS and the ability of Epo to act as a neuroprotective agent and to increase recovery rates after peripheral nerve injury as demonstrated by histological, biochemical and functional studies. The effects of Epo on peripheral nerve injury are substantially different from its effects on nerve injury in the CNS, most strikingly in the ability of Epo administered post injury to have an effect on recovery rates, pain and healing.

Three different models of peripheral nerve injury, chronic constriction injury (CCI), a model for chronic neuropathic pain (carpal) tunnel syndrome; spinal nerve crush (SNC), a model for chronic neuopathic pain; and nerve root crush (NRC), a model for lumbar radiculopathy/sensory loss, were used to investigate the effects of Epo in the peripheral nervous system (PNS). In all three models of peripheral nerve injury, systemic administration of Epo after injury was found to improve recovery rate as demonstrated by decrease apoptosis, enhanced cell number and viability, and reduced pain behaviors. The ability of Epo to have an effect on healing in the PNS when administered after injury is surprising in view of observations in the CNS. These results provide a new paradigm for the treatment of PNS injury and neuropathic pain.

Proposed mechanisms of action of Epo in neuroprotection, amelioration of pain and improved recovery rate are provided herein. However, it should be noted that these mechanisms of action are not a limitation of the invention which is the administration of a therapeutic dose of Epo as a neuroprotective agent and for the treatment of peripheral nerve injury, both to reduce pain and increase recovery rate.

In the methods of the invention, the Epo to be administered to the individual is understood to be human Epo (SEQ ID1) or an Epo mimetic, or a combination of the two in a pharmaceutically acceptable carrier depending on the route of administration. The term Epo should be understood to encompass all of these in the context of the method of the invention. A number of Epo mimetics are well known to those skilled in the art and include, but are not limited to, those referenced herein. The references typically include guidance as to the activity of the various compounds as compared to native or rhEpo by the preferred routes of administration of the compounds. However, it should be noted that optimization of dosing is a routine matter of choice and well within the ability of those skilled in the art. The Epo mimetic can be a mutated or truncated version of human Epo, such as those taught by Sytkowski et al. in U.S. Pat. No. 6,489,293 (incorporated herein by reference) or a fusion protein containing Epo fused to another protein (see Young et al., U.S. Pat. No. 6,548,653, incorporated herein by reference). Epo can be modified to contain increased numbers of oligosaccharide chains to increase the half-life and efficacy of the protein as with NESP (SEQ ID 2, MacDougall, *Semin. Nephrol.* 20:375-381, 2000, incorporated herein by reference). The Epo mimetic can be an Epo conjugate such as those taught by Burg et al. in U.S. Pat. No. 6,340,742 (incorporated herein by reference). The Epo mimetic can contain substituted or artificial amino acids, such as those taught by Connolly et al. in U.S. Pat. No. 6,310,078 (incorporated herein by reference). The Epo mimetic can be a protein or small molecule designed to bind EpoR wherein the mimetic can have little or no similarity to native Epo (see Wilson et al. U.S. Pat. No. 5,835,382, incorporated herein by reference). The Epo mimetic can be an antibody that binds to and activates EpoR (see Elliot, U.S. Pat. No. 6,319,499, incorporated herein by reference). Screens for the identification of ligands to EpoR mimetics are known (see Middletown et al. U.S. Pat. No. 6,221,608, incorporated herein by reference). Products derived from such screens can be used in the method of the invention. Epo and Epo mimetics can be administered with other agents to improve their pharmacokinetic and pharmacodynamic properties (Igari, U.S. Pat. No. 6,045,830, incorporated herein by reference). Preferred erythropoietin mimetics would be those that do not stimulate erythropoiesis while maintaining the desired effects in the nervous system. Such mimetics are well known to those skilled in the art and include the peptide included in the sequence listing (SEQ ID 3, Campana et al., *Int. J. Molec. Med.* 1:235-241, 1998).

In the method of the invention, it is preferred that the Epo is delivered by subcutaneous injection. Subcutaneous injection has been shown to be more effective than intravenous or intraperitineal injections (Fisher, *Exp Biol. Med.* 288:1-14, 2003). For example, the half life of rhEpo (recombinant human Epo) injected intravenously is about 4 hours whereas, injection by subcutaneous routes are greater than 24 hours (Egrie et al., *Kidney Int.*, 33:262, 1998). As injection of Epo can be painful, it is preferred that it is administered no more than once per day, preferably 2 to 3 times per week. A number of routes of administration are well known to those skilled in the art and can be used with the method of the invention including, but not limited to, oral and parenteral. Routes of parenteral administration are included, but not limited to subcutaneous, intravenous, intramuscular, intraperitoneal, and IT. Epo is not completely broken down in the digestive system and may be absorbed when delivered orally. It is understood that Epo mimetics can be modified or delivered with other agents to improve pharmacokinetic and pharmacodynamic properties for different routes of administration. Such considerations are well known to those skilled in the art.

When the Epo or Epo mimetic is a natural peptide, it can be expressed from a gene expression cassette containing a promoter operably linked to the coding sequence for the Epo or Epo mimetic. The expression cassette may additionally contain regulatory, replication, integration and targeting sequences. Such sequences are well known to those skilled in the art. The gene expression cassette may be delivered using viral or non-viral vectors or as naked DNA by methods known to those skilled in the art. Such a delivery system for Epo could be beneficial when long term treatment with Epo is required for the treatment of a chronic disease by ameliorating the need for regular injections.

The amount of Epo or Epo mimetic to be administered depends on a number of factors well known to those skilled in the art. Doses ranging from 1000 to 5000 units/kg body weight/day were found to be effective with doses of 2680-5000 units/kg body weight/day being more effective than the lower dose. A negative feedback loop is known to exist with Epo in pathways involved in erythropoiesis. Therefore, it is expected that a similar, negative feedback loop would be present in neuronal cells. Increased dose may be less, rather than more effective. Additional considerations in determining the optimal dose of Epo for an individual depends on considerations such as cardiac health, specifically blood pressure, and iron storage diseases, especially if the Epo being used has the ability to stimulate erythropoiesis. At day 14 after crush, rats treated with 2680 units/kg body weight per day rhEpo were found to have a significant increase in hematocrit (see Table 1). No change was seen in blood pressure. As with individuals being treated with Epo for anemia are tested regularly for changes in blood pressure, hematocrit and iron levels, individuals being treated for nerve damage and neuropathic pain should be regularly monitored for changes in these parameters and doses should be altered or other drug therapies should be included, accordingly. Such monitoring methods are well known to those skilled in the art.

The dose of Epo to be administered will vary widely on the route of administration. Doses presented herein are based on subcutaneous injection. It is understood that higher doses are required for intravenous or oral administration due to decreased bioavailability of rhEpo when delivered by such routes. Epo mimetics can be designed to increase bioavailability of the compound by various routes of administration. Determining a proper dose is a routine matter and well within the ability of those skilled in the art. A injected subcutaneous dose of rhEpo is about 50-5000 unit/kg body weight per day, with a preferred dose being about 100-5000 units/kg body weight per day with a most preferred range being 100-1000 units/kg body weight per day. Preferred dosing regimens result in the slow release of Epo over extended time as bolus doses may result in downregulation of EpoR.

The duration of treatment with Epo will vary depending on the injury or source of neuropathic pain. Treatment for an acute injury or event (e.g. spinal cord injury) would likely be short term, in the range of weeks to months. If the source of neuropathic pain is due to a chronic condition (e.g. diabetes), treatment with Epo can be for an indefinite period. Such issues are a matter of choice and within the ability of those skilled in the art.

Treatment of neuropathic pain is defined as administration of a therapeutic dose of Epo to reduce and preferably eliminate pain that results from nerve injury.

Treatment of nerve injury is defined as administration of a therapeutic dose of Epo to ameliorate injury and to increase the rate of recovery. An increased rate of recovery is defined as a reduction of indications of pain from peripheral nerve injury, such as thermal hyperalgesia and mechanical allodynia, more quickly than would be accomplished without pharmacological or other medical intervention.

Neuroprotection is defined as inhibition of cell death, typically apoptosis, in response to nerve injury as compared to that which would be observed without pharmacological or other medical intervention.

Pretreatment with Epo one day prior to nerve root crush was included in the experiments of the instant application; however, several reports have indicated that Epo preconditioning is more effective in preventing apoptosis during brain ischemia (Morshita et al., *Neuroscience* 76:105-117, 1997, and Digicaylioglu and Lipton, *Nature* 412:641-7, 2001). Moreover, recent studies have confirmed the teachings of this application showing the efficacy of Epo post-treatment after spinal cord injury and retinal ischemic trauma (Celik et al., *Proc. Natl. Acad. Sci. USA* 99:2258-63, 2002 and Junk et al., *Proc. Natl. Acad. Sci. USA* 99:10659-64, 2002). In surgical situations in which peripheral nerve injury is a reasonable possibility, pretreatment with Epo may be advisable for potential neuroprotective effects. However, as peripheral nerve injury is frequently unpredictable, initiation of treatment with a therapeutic dose of Epo as soon as reasonably possible after injury is preferred with treatment being maintained until pain abates.

The experiments of the instant application suggest that although Epo may not be initially protective, it significantly augments the recovery rate for thermal hyperalgesia and mechanical allodynia after spinal cord injury in the three models tested. Treatment with Epo was also shown to have a neuroprotective effect to nerves and satellite cells adjacent to the injured nerve in all of the models analyzed with which apoptosis is associated.

Figure 1A:
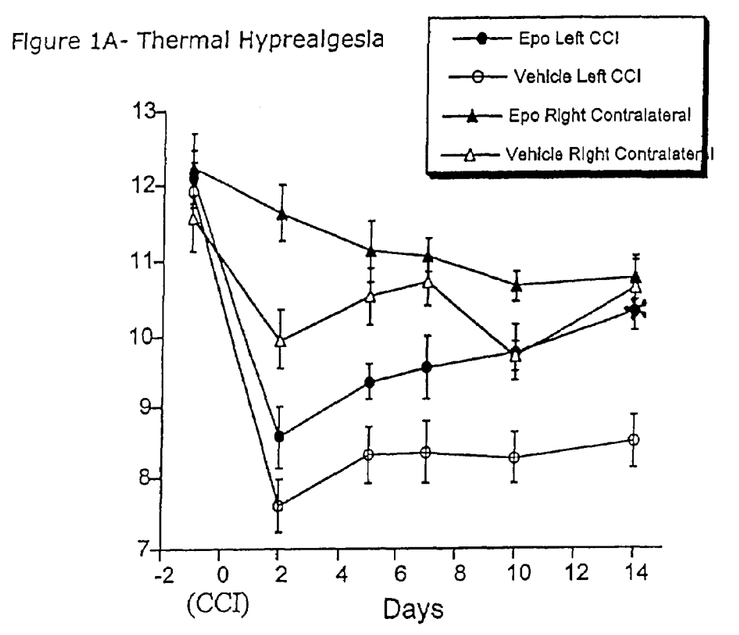
FIGS. 1A and 1B show an increased rate of recovery from thermal hyperalgesia and mechanical allodynia due to treatment with rhEpo after chronic constriction injury.
Figure 1B:
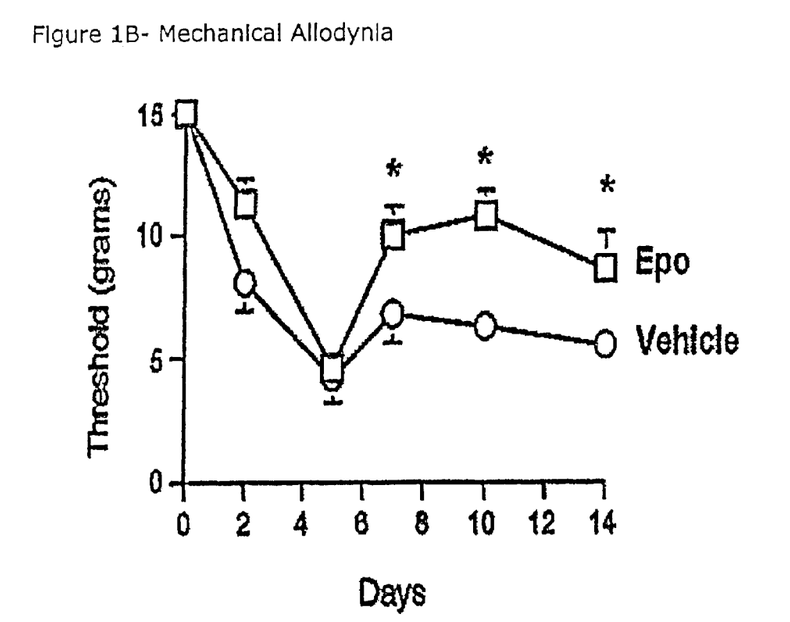

In CCI, animals were treated with 2680 units/kg body weight per day injected subcutaneously. Animals were tested for recovery rates from thermal hyperalgesia and mechanical allodynia. By days 7 and 14, allodynia and hyperalgesia were significantly decreased as compared to vehicle treated (FIGS. 1A and 1B). This demonstrates the efficacy of the administration of Epo in the treatment of CCI. The induction of apoptosis was evaluated in DRG cells after CCI by using the TUNEL assay which is well known to those skilled in the art. Little to no positive TUNEL staining was apparent in CCI animals as compared to sham-operated control animals.

Figure 2A:
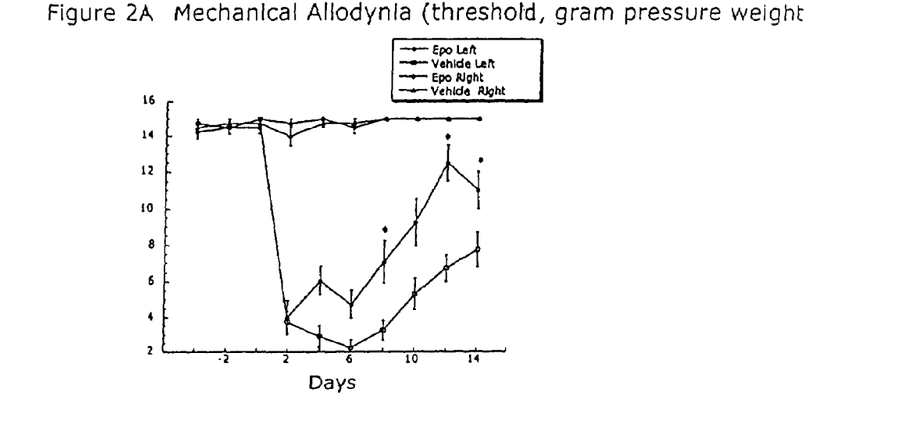
FIGS. 2A through 2C show an increased rate of recovery from mechanical allodynia (A); decreased apoptosis in both primary and sensory neurons and supporting cells (B); and no change in apoptosis in spinal neurons (C) due to treatment with rhEpo after spinal nerve crush.

In SNC, animals were treated for 18 days with 1000, 2680, 5000 units/kg body weight per day of rhEPO, or 2680 units/kg body weight per day of boiled rhEPO as a control with all Epo administered by subcutaneous injection. Approximately 75% of the boiled rhEpo and low-dose rhEpo-treated animals exhibited pain behavior identified as mechanical allodynia from day 1 to day 14 indicating effective pain relief. In the high-dose group there was some effectiveness, approximately 60% of the animals exhibited mechanical allodynia from day 1 to day 10. By day 12, the high-dose rhEpo group had only 40% of the animals exhibiting pain behavior which continued to be reduced to as low as 10% of the animals by day 18. However, the effectiveness of the high dose was not better than the middle dose of rhEpo that had been used in a complimentary study. Therefore subsequent studies were performed using the middle dose (2680 mg/kg body weight per day). FIG. 2A demonstrates that systemic treatment of rhEpo did not initially (Day 2) protect against L5 SNC-induced mechanical allodynia, but significantly (left foot rhEpo vs. left foot vehicle; $p<0.01$) enhanced recovery rates from pain behaviors one week after crush.

Figure 2B:
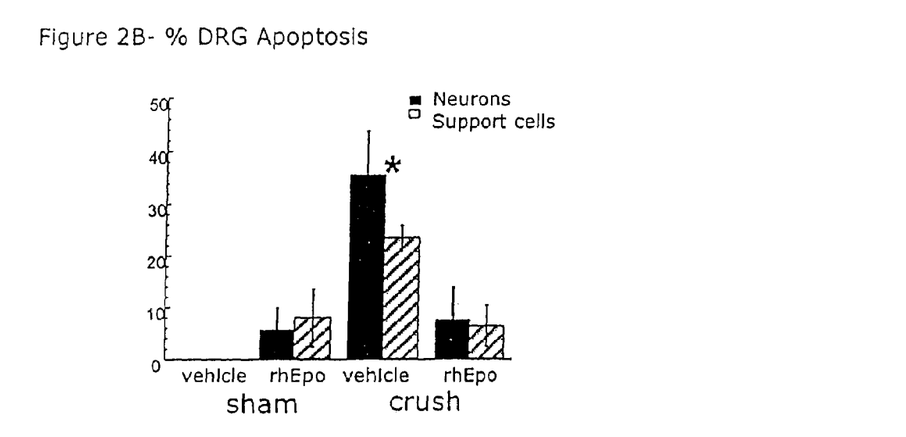

The induction of apoptosis in DRG was analyzed using immunofluorescence and confocal microscopy of TUNEL- and TOPRO-3-labeled DRG 2 days post L5 SNC. Increased TUNEL labeled nuclei of both DRG neurons and supporting cells (i.e., mostly DRG satellite cells and some endothelial cells) were observed in vehicle-treated groups after SNC compared to shams. However, after rhEpo treatment, TUNEL labeling was reduced while there were no changes in cellularity as noted by similar TOPRO-3 staining of the DRG. Quantification of apoptotic DRG neurons and support cells in sham DRGs treated with vehicle or rhEpo revealed minimal presence of apoptosis. However, there was a significant difference ($p<0.01$) in TUNEL staining between vehicle-treated, crush-injured DRGs (neurons=35.5+/−8.3%; satellite cells=23.5+/−2.36%) and rhEpo-treated, crush-injured DRGs (neurons=7.5%+/−6.3%; satellite cells=6.4+/−3.94%) (FIG. 2B).

Figure 2C:
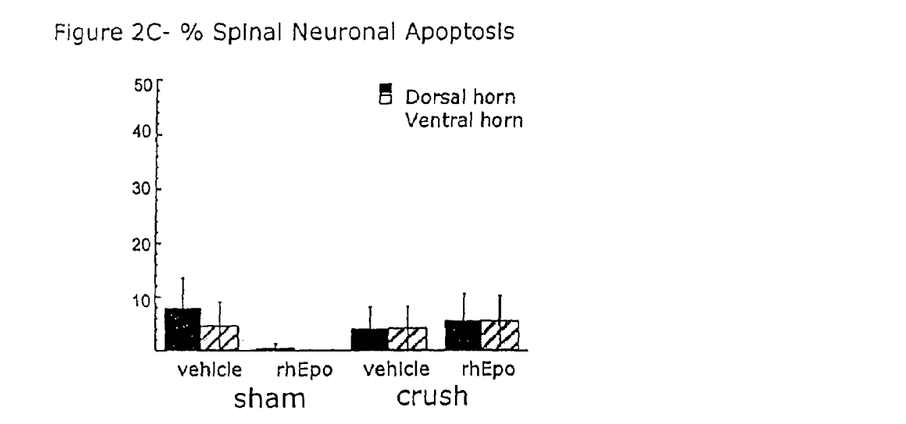

Quantification of apoptotic spinal neurons by ISOL, a method that follows the appearance of DNA strand breaks and distinguishes between apoptotic and necrotic neurons, in the ipsilateral superficial dorsal and ventral horn revealed no significant increases in apoptosis 2 days after SNC in either the vehicle or rhEpo treated groups (FIG. 2C).

Figure 3A:
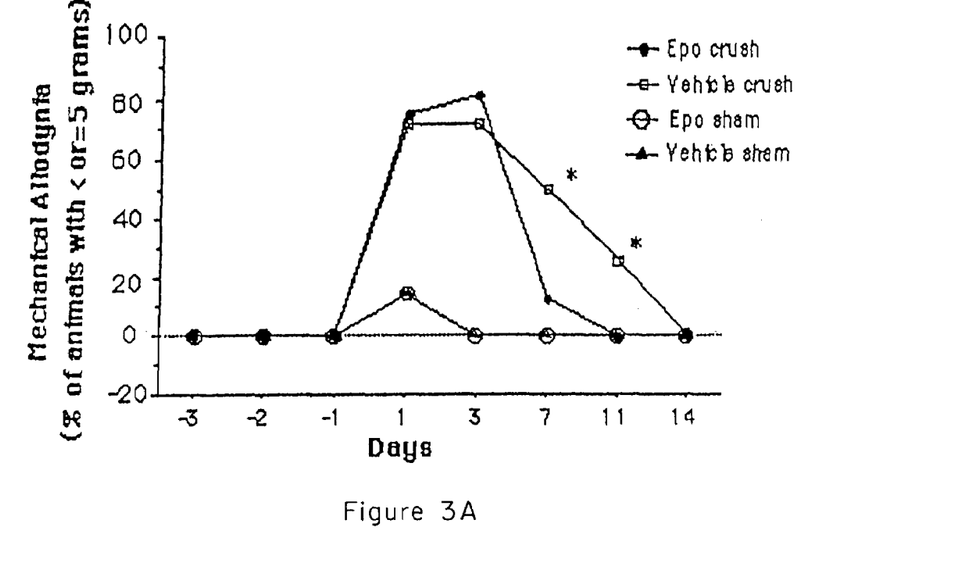
FIGS. 3A and 3B show an increased rate of recovery from mechanical allodynia due to treatment with rh Epo after nerve root crush.
Figure 3B:
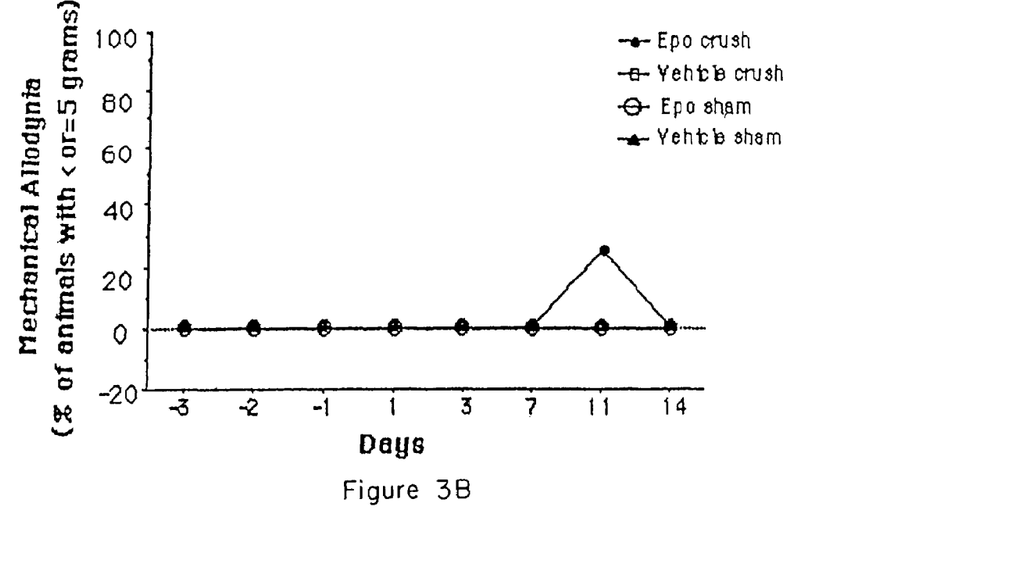

In NRC, animals were treated for 14 days with 2680 units rhEpo/kg body weight per day. Approximately 80% of ipsilateral hindpaws exhibited mechanical allodynia 1 and 3 days post NRC (FIG. 3A-FIG. 1A from Spine). This was apparent in both Epo-(2680 units/kg body weight per day) and vehicle-treated crush groups. In contrast, only 14.3% of ipsilateral hindpaws in the sham-operated group demonstrated allodynia 1 day post crush. By day 7, 50% of ipsilateral hindpaws in the vehicle-treated animals still exhibited allodynia whereas, the Epo-treated crush animals only had 12.5% of ipsilateral hind paws exhibiting allodynia. The effects of Epo were subsequently sustained throughout the experimental period (day 14). At day 14, the vehicle-treated crush group also returned to baseline. Contralateral paws demonstrated little to no allodynia response with or without nerve root crush injury (FIG. 3B).

To determine whether the effects of Epo were correlated with its known neuroprotective activity, ISOL was performed to identify apoptotic neurons in lumbar spinal tissue corresponding to L5. There was an increase in ISOL positive neurons as compared to ISOL negative neurons in both the superficial dorsal and ventral horn of vehicle-treated spinal cords. In contrast, Epo-treated animals demonstrated more green staining viable neurons than brown staining apoptotic neurons in both the dorsal and ventral horn demonstrating the neuroprotective effects of Epo.

Figure 4A:
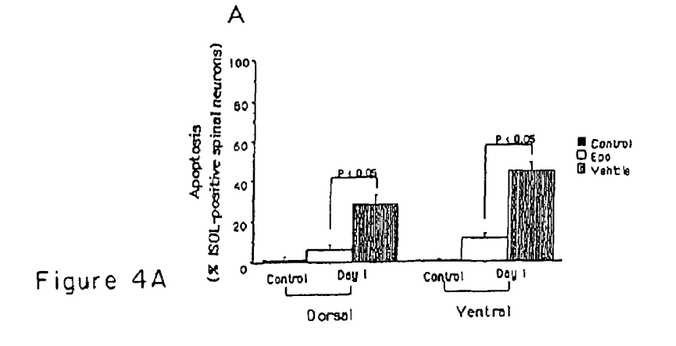
FIGS. 4A-D show decreased apoptosis due to treatment with rhEpo after nerve root crush; and The present invention will be better understood from the following detailed description of an exemplary embodiment of the invention, taken in conjunction with the accompanying drawings.
Figure 4B:
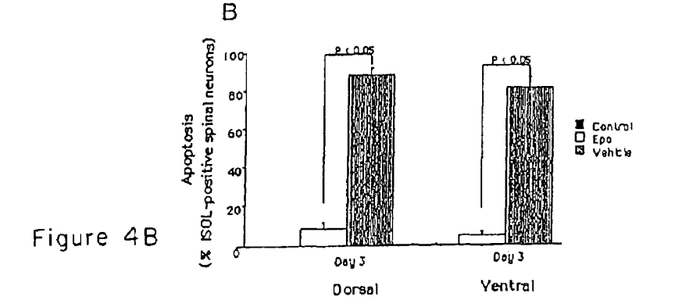
Figure 4C:
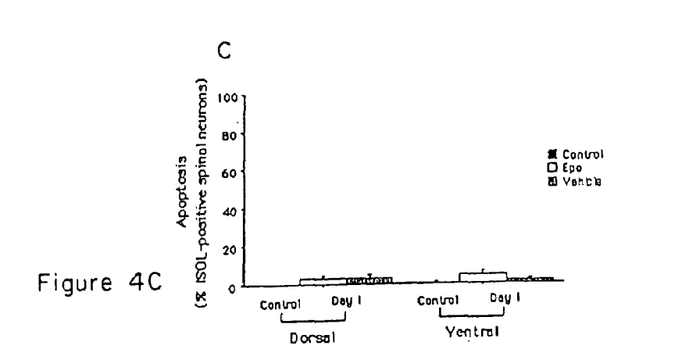
Figure 4D:
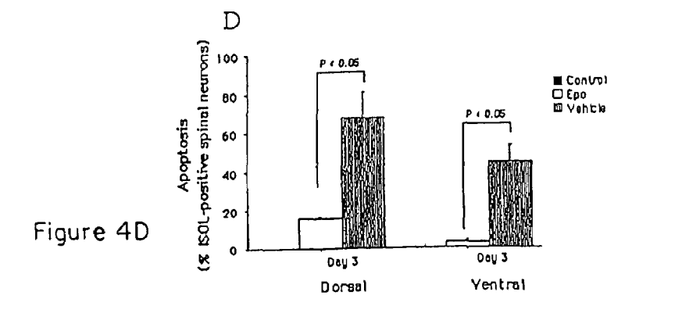

Quantification of apoptotic spinal neurons in ipsilateral superficial dorsal and ventral horns revealed a significant increase, 25% and 40%, respectively, in the number of apoptotic neurons in vehicle-treated animals one day following crush compared to uninjured animals (FIG. 4A). By day 3, the percentage of apoptotic neurons increased to approximately 80% in both superficial dorsal and ventral horn. In contrast, there was a significant reduction in apoptotic neurons in Epo-treated animals 1 and 3 days post nerve root crush in both dorsal and ventral horns (FIGS. 4A and 4B). Quantification of apoptotic neurons in the contralateral spinal cord surprisingly revealed a 65% increase in apoptotic neurons within the superficial dorsal horn and a 45% increase in ventral horn neurons 3 days post nerve root crush (FIGS. 4C and 4D).

The ability of Epo to increase recovery rates suggest that it does not inhibit aberrant electrical firing after nerve damage, but may rescue neuronal tissue at risk of dying in secondary processes such as damage by abnormally high extracellular glutamate concentrations. The latter timing of Epo effects supports a role for Epo in stimulating intracellular signaling cascades and gene transcription during Wallerian degeneration, facilitating neuroprotection. It is interesting that Epo effects corresponded to late stages of neuropathic pain behaviors and more specifically, at a time when prolinflammatory cytokines are produced. The instant application also demonstrates that in a radiculopathy and chronic constriction injury models associated with protracted pain states, Epo downregulated TNF produced by motor neurons and Schwann cells, indicating that Epo may be involved in regulating pain-producing cytokines.

EXAMPLE 1

Immunofluorescence and identification of erythropoietin in DRG and sciatic nerve. To identify the presence of Epo in the peripheral nerve, immunohistochemical analysis of sciatic nerve sections of rats with and without CCI injury was performed. Animals were perfused transcaudally through the ascending aorta with 4% paraformaldehyde in 0.1 M phosphate buffered saline (PBS) at postoperative days 1, 3, 5, and 7 (n=4 for each time point). Nerve segments taken from sciatic nerves and dorsal root ganglia (DRG) obtained from rats before and after injury were fixed briefly in 4% paraformaldehyde and subsequently embedded in paraffin. Sections, 10-μm-thick, were incubated with primary antibodies (anti-Epo 1:100, anti-EpoR 1:5000) overnight at 4° C. Secondary antibodies of the appropriate species tagged with either FITC or rhodamine were used. Imaging was performed using a laser-scanning confocal microscope using methods well known to those skilled in the art.

In the normal nerve, using an anti-Epo polyclonal antibody, immunoreactive material was present in axoplasm and in a few Schwann cell crescents. Epo was present in approximately ⅓-½ of normal DRG neurons and stained both nuclear and cytoplasmic spaces in both small and large neurons. After 5 days of CCI, less Epo immunoreactivity was noted in axoplasm, yet Schwann cells demonstrated enhanced immunoreactivity for Epo.

EXAMPLE 2

Identification of erythropoietin receptor in the sciatic nerve after CCI. The presence of EpoR in uninjured and injured sciatic nerve was also investigated. In uninjured nerve, EpoR was localized in the axoplasm, Schwann cell crescents, and inner glial loops and in endothelial cells. After CCI injury, a similar cell distribution of EpoR immunostaining was observed, however, there was slightly less staining of the axoplasm.

EXAMPLE 3

EpoR immunostaining in DRG. Immunostaining of EpoR in DRGs of normal rats revealed the presence of EpoR on many cell bodies. Generally, a large proportion of EpoR was present in the cytoplasmic portion of the DRG cell bodies. However, with higher concentrations of anti-EpoR (1:500), distinct punctate staining at the plasma membrane was observed and confirmed with two other EpoR antibodies. After two different injuries, CCI in the sciatic nerve and crush distal to the DRG, the proportion of EpoR immunostaining in DRG cell bodies changed only in the crush model (Table 2). Table 2 shows the significant reduction of EpoR after 7 days of adjacent crush injury compared with day 0 controls. These findings were identified by a 2D assumption-based cell counting approach and are conservative as they are based on absolute loss of EpoR staining (i.e., no brown staining). Less intense staining of EpoR in neurons was noted. These results were further confirmed by analyzing the DRG homogenates from day 0 and day 7 in crush-injured animals. Homogenates containing equal amounts of protein from injured or uninjured DRGs were immunoprecipitated and Western blotted by using an anti-EpoR antibody. EpoR was identified at a molecular weight of approximately 70 kDa and 90 kDa. Immunoprecipitates from adjacent crush-injured rats contained less EpoR (both the 70 kDa and 90 kDa protein) than that in uninjured rats. The blots were also probed with anti-phosphotyrosine antibodies and observed that after distal crush injury, phosphorylation of the 90 kDa band was greater than the 70 kDa band.

EXAMPLE 4

Nerve crush. Adult female Sprague-Dawley rats weighing 200 to 250 g were used in this study (n=4 animals per timepoint), which was approved by the local Animal Studies Committee. Animals were anesthetized by intraperitoneal injection of a solution containing sodium pentobarbital (Nembutal, 50 mg/ml; Abbott Laboratories, Chicago, Ill.), diazepam (5 mg/ml; Steris Laboratories, Phoenix, Ariz.), and saline (0.9%; Steris Laboratories, Phoenix, Ariz.) in volume proportion of 1:1:2, respectively. Initially, 0.5 ml was injected and then supplemented with 0.1 ml injections as needed to produce an adequate level of surgical anesthesia throughout the experiment.

Through a midline incision, the thoracolumbar fascia was incised just left of the spinous processes of the fifth and sixth lumbar vertebrae. The sacrospinalis muscle was gently moved laterally to expose the facet joint between the fifth and sixth lumbar vertebrae. The L5 nerve root, DRG, and spinal nerve were exposed by L5/6 facectomy and L5 hemilaminectomy, using great care to avoid trauma to the tissue. The L5 nerve proximal to (in nerve root crush) or just distal (2 mm) from (in spinal nerve crush) the DRG was crushed once for 2 s, by using a smooth surface forceps. We intended that some nerve fibers would survive the crush and that sensory function would not be blocked completely. In fact, this form of proximal nerve injury produces a transient hyperalgesia and neuronal apoptosis. Other animals, in which the spinal nerve was exposed but not crushed, were used for controls (sham surgery).

EXAMPLE 5

Chronic constriction injury. Under barbiturate anesthesia, the sciatic nerve was exposed unilaterally at the midthigh level. Four ligatures (chromic gut 4.0) were placed around the nerve with 1-mm spacing. The ligatures were tied until they constricted, just slightly, the diameter of the nerve and a brief twitch was seen in the respective hind limb. This finding is associated with an approximate 50% reduction in nerve blood flow. Four animals per timepoint were used with contralateral and uninjured nerves serving as controls. The wound was closed in layers. Thermal hyperalgesia has been shown to be a reliable indicator of pain-related behavior in this model.

EXAMPLE 6

Behavioral testing for thermal hyperalgesia. The thermal nociceptive threshold was measured in each hindpaw of the experimental animals before surgery and at regular intervals from day 1 after surgery using a thermal testing device and protocol that allowed each animal to serve as its own control (Hargreaves et al., *Pain* 32:77-78, 1988). This technique uses a light source to selectively heat one foot at a time rather than heating both feet simultaneously. The method is ideally suited for investigations of neuropathic pain involving unilateral lesions to peripheral nerves. Both the left (injured) and right (uninjured) footpads were tested as described previously (Wagner R. Myers R R., *Neuroreport* 7:2897-901, 1996).

All animals were tested for three consecutive days prior to surgery to acclimate the animals to the testing procedure. All behavior measurements were made at the same time each day in a quiet room and by an investigator blinded to treatment groups.

EXAMPLE 7

Behavioral testing for mechanical allodynia. Sensitivity to non-noxious mechanical stimuli was tested by determining the hindpaw withdrawal response to von Prey hair stimulation of the plantar surface of the footpad (Igarashi et al., *Spine* 25:2975-80, 2000). Rats were acclimated to being on a suspended 6-mm wire grid and having the plantar surface of their footpads stimulated with von Prey filaments. Three days prior to surgery, animals were baselined to acclimate animals to movements and foot poking. After surgery, nine filaments calibrated between 1-15 g force were applied to the paw surface just until the filament bent, for a total of two applications approximately 2 to 3 seconds apart and varied in location so as to avoid sensitization. If the rat did not withdraw its foot after either of the two applications of a given filament, the next stiffer filament was tested in the same manner. When the rat withdrew its foot, the measurement was verified by ensuring that there was an absence of response at the next less stiff filament. The gram force of the filament causing the positive response was recorded for first reaction. After 5 minutes the same procedure was performed again. Baseline testing was performed three days prior to the start of the experiment to accommodate the animals to the testing procedure and to verify that they had normal responses. If the rat withdrew its foot, this gram force was recorded as a second reaction. A positive responder was identified as an animal responding to a filament gram force of less than 5 grams. Crush and sham animals were tested on 1, 3, 7, 11, and 14 days after surgery.

EXAMPLE 8

Statistical analysis. Behavior data was evaluated as the number of animals that display thermal hyperalgesia, mechanical allodynia or not. Statistical analysis utilizing a 2×2 contingency table and Bonferonni Correction were performed on non-parametric data.

In NRC experiments, data are expressed as percentages. Comparisons of the number of apoptotic neurons were performed by using paired comparisons followed by a least significant difference paired t-test (Stat View 5.0). Values associated with $p<0.05$ were considered statistically significant. Data are expressed as mean ±SE.

In CCI and SNC, all studies were performed using coded animal numbers to avoid observer bias. Behavioral data were analyzed by ANOVA for repeated measures. In some data sets where significant differences were indicated, ANOVA with Scheffe's post hoc analysis was used to detect deficiencies within treatment groups between treatment groups each day. Apoptosis data were analyzed by a one-way ANOVA and, if significant ($p<0.05$), treatment means were compared by Tukey's post hoc test. Hematocrit, blood pressure and weight were independently tested for significance by a t-test at day 14.

Although an exemplary embodiment of the invention has been described above by way of example only, it will be understood by those skilled in the field that modifications may be made to the disclosed embodiment without departing from the scope of the invention, which is defined by the appended claims.

---

We claim:

1. A method for reducing neuropathic pain in an individual suffering from neuropathic pain comprising administering an amount of erythropoietin (Epo) to the individual, effective to reduce neuropathic pain and reducing neuropathic pain in the individual.

2. The method of claim 1, wherein the Epo is rhEpo.

3. The method of claim 2, wherein rhEpo is administered by subcutaneous injection.

4. The method of claim 3, wherein rhEpo is administered at a dose of about 500 to 5000 units/kg body weight per day.

5. The method of claim 3, wherein rhEpo is administered at a dose of about 100 to 5000 units/kg body weight per day.

6. The method of claim 3, wherein the rhEpo is administered at a dose of about 100-1000 units/kg body weight per day.

7. The method of claim 1, wherein the Epo is administered by a route selected from a group consisting of oral and parenteral.

8. A method for reducing a neuropathic pain in an individual suffering from nerve injury and pain comprising administering an amount of erythropoietin (Epo) to the individual, effective to reduce neuropathic pain in the individual and reducing neuropathic pain in the individual.

9. The method of claim 8, wherein the Epo is rhEpo.

10. The method of claim 9, wherein rhEpo is administered by subcutaneous injection.

11. The method of claim 10, wherein rhEpo is administered at a dose of about 50 to 5000 units/kg body weight per day.

12. The method of claim 10, wherein rhEpo is administered at a dose of about 100 to 5000 units/kg body weight per day.

13. The method of claim 10, wherein the rhEPO is administered at a dose of about 100-1000 units/kg body weight per day.

14. The method of claim 8, wherein the Epo is administered by a route selected from a group consisting of oral and parenteral administration.

15. The method of claim 8, wherein the nerve injury induces neuralgia, lumbar radiculopathy, vasculitis, peripheral nerve injury, chronic constriction injury (CCI), carpal tunnel syndrome; or lumbar radiculopathy/sensory loss.

16. The method of claim 1 or 8 further comprising identifying an individual suffering from neuropathic pain before administering the Epo.

* * * * *

SEQUENCE LISTING

```
<160> NUMBER OF SEQ ID NOS: 3

<210> SEQ ID NO 1
<211> LENGTH: 166
<212> TYPE: PRT
<213> ORGANISM: Homo sapiens

<400> SEQUENCE: 1

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
        50                  55                  60

Gln Gly Leu Ala Leu Leu Ser Glu Ala Val Leu Arg Gly Gln Ala Leu
65                  70                  75                  80
```

-continued

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Arg Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 2
<211> LENGTH: 166
<212> TYPE: PRT
<213> ORGANISM: Artificial
<220> FEATURE:
<223> OTHER INFORMATION: modified human sequence

<400> SEQUENCE: 2

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Asn Glu Thr
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
        50                  55                  60

Gln Gly Leu Ala Leu Leu Ser Glu Ala Val Leu Arg Gly Gln Ala Leu
65                  70                  75                  80

Leu Val Asn Ser Ser Gln Val Asn Glu Thr Leu Gln Leu His Val Asp
                85                  90                  95

Lys Ala Val Ser Gly Leu Arg Ser Leu Thr Thr Leu Leu Arg Ala Leu
                100                 105                 110

Arg Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 3
<211> LENGTH: 16
<212> TYPE: PRT
<213> ORGANISM: Artificial
<220> FEATURE:
<223> OTHER INFORMATION: modified human sequence

<400> SEQUENCE: 3

Glu His Cys Ser Leu Asn Glu Asn Ile Thr Val Pro Asp Thr Lys Val
1               5                   10                  15